United States Patent
Xiao

(10) Patent No.: US 11,052,232 B2
(45) Date of Patent: Jul. 6, 2021

(54) DEVICES FOR APPLYING LIQUID TO SKIN

(71) Applicant: Long Xiao, Scarborough (CA)

(72) Inventor: Long Xiao, Scarborough (CA)

(*) Notice: Subject to any disclaimer, the term of this patent is extended or adjusted under 35 U.S.C. 154(b) by 250 days.

(21) Appl. No.: 16/504,066

(22) Filed: Jul. 5, 2019

(65) Prior Publication Data

US 2020/0023175 A1    Jan. 23, 2020

(30) Foreign Application Priority Data

Jul. 17, 2018   (CA) .................. CA 3011593

(51) Int. Cl.
*A61M 37/00*   (2006.01)

(52) U.S. Cl.
CPC ... *A61M 37/0084* (2013.01); *A61M 2209/082* (2013.01)

(58) Field of Classification Search
CPC ... A61M 37/0076–0084; A01K 11/005; A61B 17/34; A61B 17/3494; A61B 17/3496; A61B 17/3409; A61B 5/150412; A61B 5/15146; A61B 5/1411; A61B 5/15192
USPC .................................. 606/116, 186
See application file for complete search history.

(56) References Cited

U.S. PATENT DOCUMENTS

| | | | |
|---|---|---|---|
| 6,345,553 B1* | 2/2002 | Adler ................. | A45D 34/04 30/362 |
| 6,505,530 B2 | 1/2003 | Adler et al. | |
| 8,029,527 B2 | 10/2011 | Lisec | |
| 2005/0197620 A1* | 9/2005 | Tu ................. | A61B 17/3421 604/26 |
| 2009/0183602 A1 | 7/2009 | Crockett | |
| 2010/0206138 A1 | 8/2010 | Clark | |
| 2011/0048174 A1 | 3/2011 | Lin | |
| 2012/0041374 A1 | 2/2012 | Lee | |

(Continued)

FOREIGN PATENT DOCUMENTS

| | | |
|---|---|---|
| CA | 2917187 A1 | 1/2015 |
| CN | 2356645 Y | 1/2000 |

(Continued)

OTHER PUBLICATIONS

Extended European Search Report dated Feb. 4, 2019 in related EP Patent Application No. 18191616.4.

*Primary Examiner* — Darwin P Erezo
*Assistant Examiner* — Brigid K Byrd

(57) ABSTRACT

A needle assembly for a liquid applicator comprises housing with longitudinal channel. The channel comprises upper and lower open ends. A needle bundle is movably mounted in the channel, which comprises needle shaft and needles attached thereto. A biasing member is configured and mounted for (i) biasing the needle bundle longitudinally towards a retracted position and (ii) biasing the needles laterally towards a needle-guiding side wall of the housing adjacent the lower open end. The biasing member is configured and mounted to form a fluid seal between the lower and upper open ends. The biasing member comprises an elastic tubular section with opposite sides. The first side has a first rectified length. The second side has a second rectified length longer than the first rectified length so that the second side is less tensioned than the first side to bias the needles towards the needle-guiding side wall.

24 Claims, 15 Drawing Sheets

(56) References Cited

U.S. PATENT DOCUMENTS

| | | | |
|---|---|---|---|
| 2012/0192681 A1* | 8/2012 | Klebs | A61M 37/0076 81/9.22 |
| 2015/0151098 A1* | 6/2015 | Spendlove | A61M 37/0076 606/186 |
| 2015/0352346 A1 | 12/2015 | Webb | |
| 2016/0184572 A1 | 6/2016 | Xiao | |

FOREIGN PATENT DOCUMENTS

| | | |
|---|---|---|
| CN | 201595866 U | 10/2010 |
| CN | 106902452 A | 6/2017 |
| EP | 2420265 A2 | 2/2012 |
| EP | 2896427 A1 | 7/2015 |

* cited by examiner $F_A = F_{1A} + F_{2A}$
$F_R = F_{2R} - F_{1R}$

DEVICES FOR APPLYING LIQUID TO SKIN

CROSS-REFERENCE TO RELATED APPLICATIONS

This application claims the benefit of, and priority from, Canadian Patent Application No. 3,011,593, filed Jul. 17, 2018, entitled "DEVICES FOR APPLYING LIQUID TO SKIN", the entire contents of which are incorporated herein by reference.

FIELD

The present invention relates generally to devices for applying a liquid to skin, particularly to devices such as tattooing devices or devices for applying permanent make-up.

BACKGROUND

A tattooing device typically includes a needle for applying ink to skin, a base with a needle actuator, and a needle handle that connects the needle to the base and can be conveniently held in a hand of an operator for manipulating the needle during use. In operation, the tattooing needle is actuated by the needle actuator to reciprocatively move between extended and retracted positions, thereby repeatedly puncturing the subject's skin. Tattoo needles may be attached to the needle handles directly as in traditional tattooing devices, or may be provided in a needle module, which is attached to the needle handle. Examples of tattooing devices include rotary tattooing machines and coil tattooing machines. In cases where a needle module is used, the tattooing machine is typically configured such that the needle actuator applies a downward force via a drive shaft to push the needles downward towards the extended position, but will not apply an upward force to pull the needles back to the retracted position. Instead, an elastic member is provided in the needle module to pull the needles back to the retracted position.

Ink may be stored in an ink reservoir and may be fed to the tattoo needle and thence to the subject's skin.

For safety reasons, the needle is typically sterilized before use and replaced after each use. It is thus convenient to use replaceable and disposable needle modules, which can be pre-sterilized and easily detached or connected to the needle handle so that the needle can be easily replaced, and safely disposed.

Devices or applicators for applying permanent mark-up may have a similar construction, with a base, a replaceable handle, and a replaceable/disposable needle module.

However, there is still a risk that bodily fluids, such as blood or serum, issued from the punctured skin of a subject will come into contact with the needle handle or base of the tattooing device, and subsequently with the operator of the device.

CN106902452A by Wang, published Jun. 30, 2017 disclosed a tattoo device, which includes a shell, a needle and an elastic membrane. A linkage structure is arranged on the needle and fixedly connects the needle with the elastic membrane. A restoring force generated by the elastic membrane acts on the needle to move the needle backwards to return it to a retracted position. The elastic membrane further generates a force for moving the needle towards an operation section of the shell.

It is still desirable to improve the above and other existing tattoo devices for applying ink or another liquid to skin.

SUMMARY

An aspect of the present disclosure relates to solving one or more problems present in existing tattooing needle modules where a silicone tubing is used to both bias the needles longitudinally and laterally and to form a seal between the lower portion of the needle module and the upper portion of the needle module.

For example, it has been recognized that one of the problems with the use of such a silicone tubing is that it is difficult to select a suitable thickness for such a tubing. If the tubing wall is too thin, the seal is not secure as the tubing wall may break or puncture when it is stretched during operation. If the tubing wall is thick enough to provide a secure seal, it generates a large tension force when stretched, thus requiring a large driving force to overcome the tension force and drive the needle downward. To provide a larger driving force requires more power and energy. Operating a device with more power may generate more heat, and wear and tear, which may in turn reduce the useful lifetime of the device or its components. Excess heating of the device can also cause discomfort to the user. Using silicone tubing having opposite side walls with different thicknesses to also provide the lateral biasing force would further exacerbate the problem, as the side wall on one side has to be thicker than the minimum thickness required to provide a safe and secure seal.

To address one or more of these problems, in an embodiment of the present disclosure, a biasing and sealing member is provided which comprises an elastic tubing section, where tubing section has two opposite sides with different rectified lengths. When the shorter side is stretched and tensioned during operation, a smaller tension or no tension is produced in the longer side. Thus, the driving force required to drive the needle can be significantly reduced at the same tubing wall thickness. Further, a lateral biasing force is provided even if the tubing wall has a uniform thickness. Conveniently, less power and energy is required to drive the needle and overheating may be avoided.

In accordance with an aspect of the disclosure, there is provided a needle assembly for a liquid applicator, comprising a housing comprising a longitudinal channel, the channel comprising an upper open end and a lower open end; a needle bundle movably mounted in the channel to reciprocatively move between a retracted position and an extended position, the needle bundle comprising a needle shaft and a plurality of needles attached to the needle shaft, the needles positioned to extend through the lower open end of the channel when the needle bundle is in the extended position, the needle shaft received in the upper open end of the channel for driving the needle bundle longitudinally; a biasing member configured and mounted for (i) biasing the needle bundle longitudinally towards the retracted position and (ii) biasing the needles laterally towards a needle-guiding side wall of the housing adjacent the lower open end, the biasing member being further configured and mounted to form a fluid seal between the lower open end and the upper open end, wherein the biasing member comprises an elastic tubular section having a first side and a second curved side opposite the first side, the first side of the elastic tubular section facing the needle-guiding side wall and having a first rectified length, the second side of the elastic tubular section having a second rectified length longer than the first rectified length so that the second side is less tensioned than the first side to bias the needles towards the needle-guiding side wall. The elastic tubular section may have a substantially uniform wall thickness. The first side of the elastic tubular section of the biasing member may have a first wall thickness, and the second side of the elastic tubular section of the biasing member may have a second wall thickness less than the first wall thickness. The second side of the elastic tubular section of the biasing member may be at least partially corrugated. The elastic tubular section of the biasing member may have a first end and a second end, and the biasing member may comprise a first end portion attached to the first end of the elastic tubular section and a second end portion attached to the second end of the elastic tubular section, each one of the first and second end portions having a central opening, the needle shaft extending through the central opening. The needle shaft may sealingly engage the central opening of the first end portion of the biasing member, and the second end portion of the biasing member may be sealingly affixed to the housing so that when the needle bundle moves towards the extended position. The elastic tubular section of the biasing member may be tensioned to bias the needle bundle towards the retracted position and bias the needles to contact the needle-guiding side wall. The first end portion of the biasing member may comprise a circumferential groove to reduce tension in the first end portion. The first end portion of the biasing member may have a generally polygonal cross-sectional profile. The polygonal cross-sectional profile may a square cross-sectional profile. The needle bundle may have a key profile around the needle shaft and the central opening of the first end portion of the biasing member may define a keyhole engaged with the key profile of the needle bundle. The needle bundle may comprise a key shoulder adjacent the key profile, the key shoulder abutting the first end portion of the biasing member so that the biasing member biases the key shoulder and the needle bundle towards the upper open end of the housing. The housing may comprise a removable annular cap at the upper open end of the channel, the cap engaging the second end portion of the biasing member to affix the second end portion to the housing, the cap comprising a central opening, the needle shaft passing through the central opening of the cap. The housing may comprise a first keyway at the upper open end, the second end portion of the biasing member comprises a second keyway, and the cap comprises a first key profile coupled with the first keyway of the housing and a second key profile coupled with the second keyway of the biasing member. The upper open end of the housing comprises an internal annular ridge and the cap may comprise an annular groove coupled to the annular ridge to hold the cap in position. Each one of the first and second end portions of the biasing member may have a wall thickness larger than the first and second wall thicknesses, and is more rigid than the elastic tubular section. The biasing member may form a diaphragm seal between the lower open end and the upper open end of the housing. In some embodiments, the first side of the elastic tubular section may be substantially linear. In some other embodiments, at least a portion of the first side of the elastic tubular section may be curved. The biasing member may comprise a silicone material, latex or a rubber. The biasing member may comprise a material with a Shore hardness from 30 A to 50 A. The housing may comprise a liquid storage groove at the needle-guiding wall adjacent the lower open end. The needle assembly may be configured to apply tattoo or permanent make-up to skin. The needle assembly may be a disposable module.

In another aspect there is provided a liquid applicator comprising a needle assembly as described herein. The liquid applicator may further comprise a needle actuator, and a handle coupling the needle actuator to the needle assembly.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure.

DETAILED DESCRIPTION

An embodiment of the present disclosure relates to a liquid applicator for applying a liquid to skin. The liquid applicator may be an ink applicator, such as a tattooing device 60 as illustrated in FIGS. 1A and 1B.

Figure 1A:
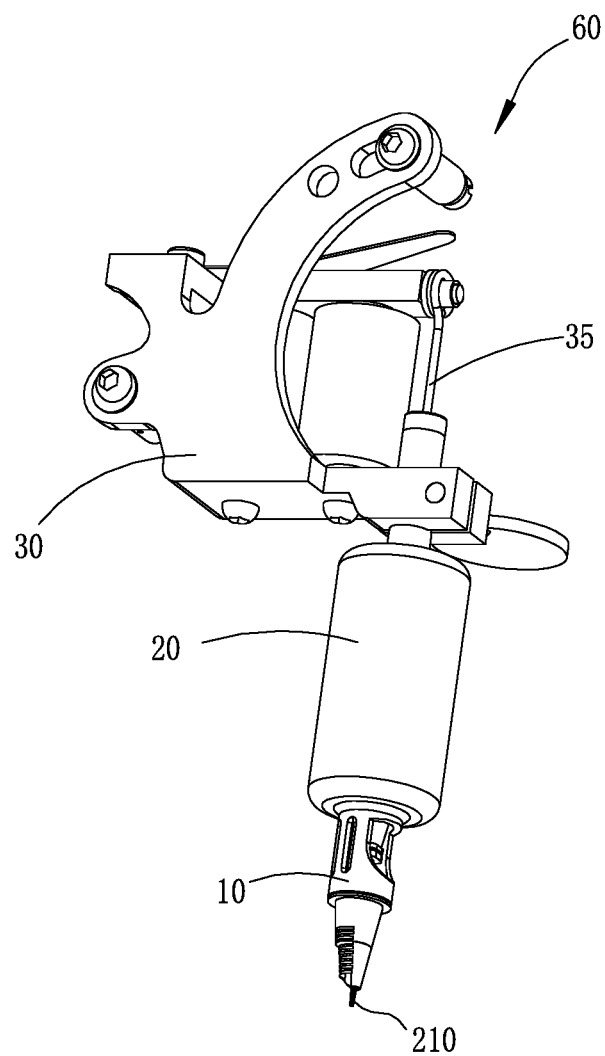
FIG. 1A is a perspective view of a tattooing device, illustrative of an embodiment of the present disclosure.
Figure 1B:
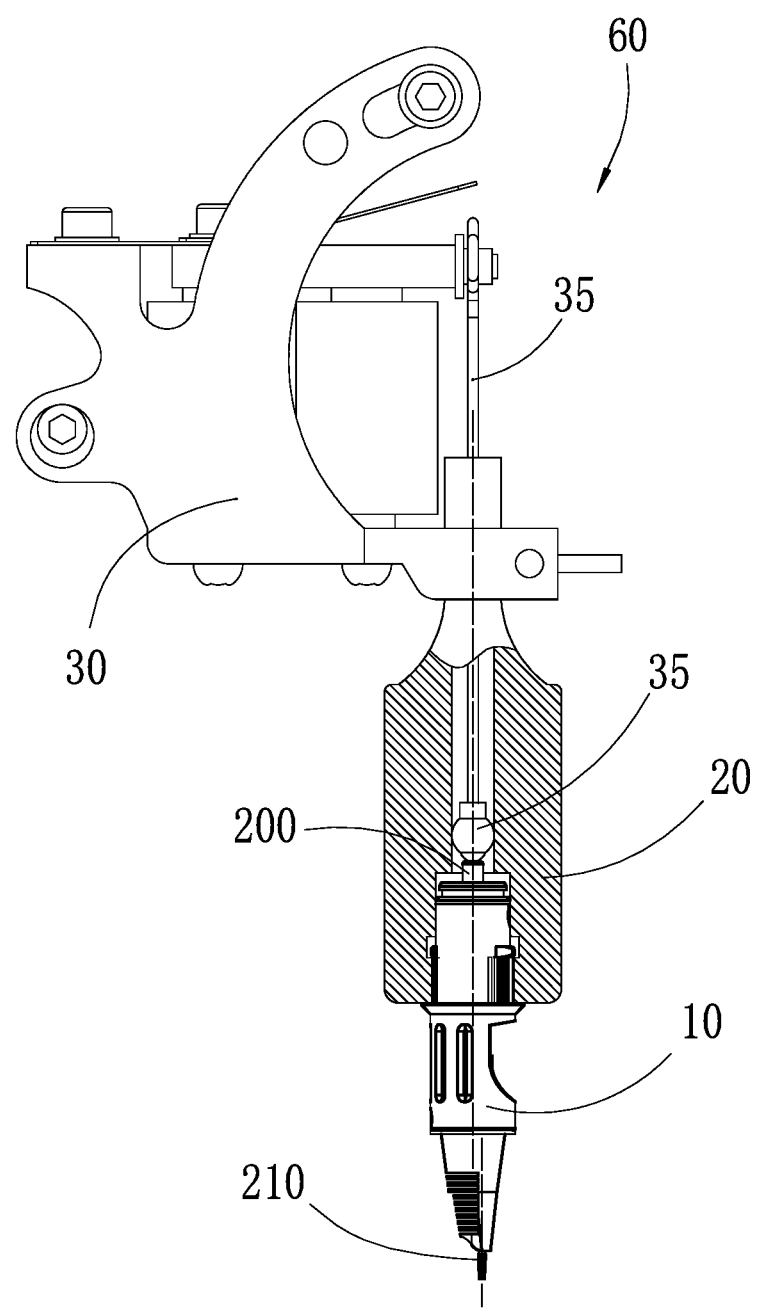
FIG. 1B is a side elevation view of the tattooing device of FIG. 1A, with partial cutaway cross-section view of the needle handle and needle module in the tattooing device.

As depicted in FIGS. 1A and 1B, the tattooing device 60 includes a needle module 10, which is coupled by a needle handle 20 to a base device 30. The needle module 10 may be a disposable needle module and the needle module 10 and the needle handle 20 may be configured to be removably coupled to each other.

The needle module 10 includes a reciprocatively movable needle bundle 200 with a needle tip portion 210 for applying ink to the skin of a subject.

The base device 30 includes a needle actuator (not separately shown) with a drive shaft 35 for actuating downward movement of the needle bundle 200.

The handle 20 has a generally tubular shape, which may be cylindrical as illustrated in the figures. A tubular shape has an inner opening or channel but is not necessarily cylindrical or has a circular cross-section, and does not have to have equal cross-sectional size along its length.

The construction and operation of the handle 20 and base device 30 are known in the art and can be similar to, for example, the corresponding parts disclosed in U.S. patent application Ser. No. 15/691,125 by Xiao, the entire contents of which are incorporated herein by reference. As such, these parts and their operation are not described in detail herein.

Figure 2A:
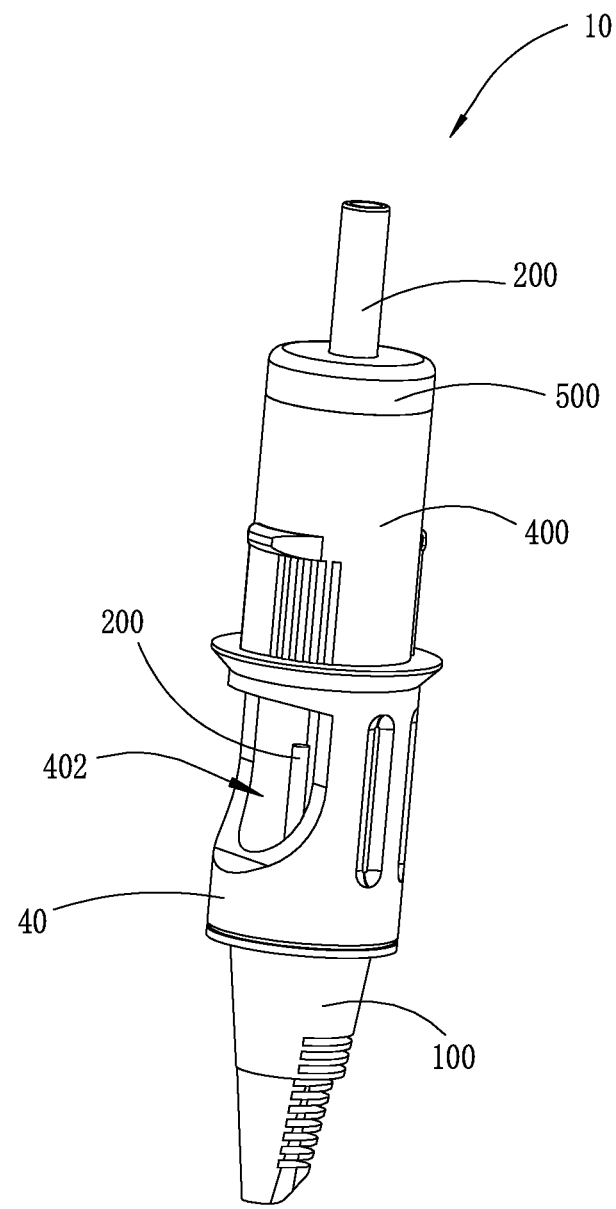
FIG. 2A is a perspective view of a disposable needle module, illustrative of an embodiment of the present disclosure.
Figure 2B:
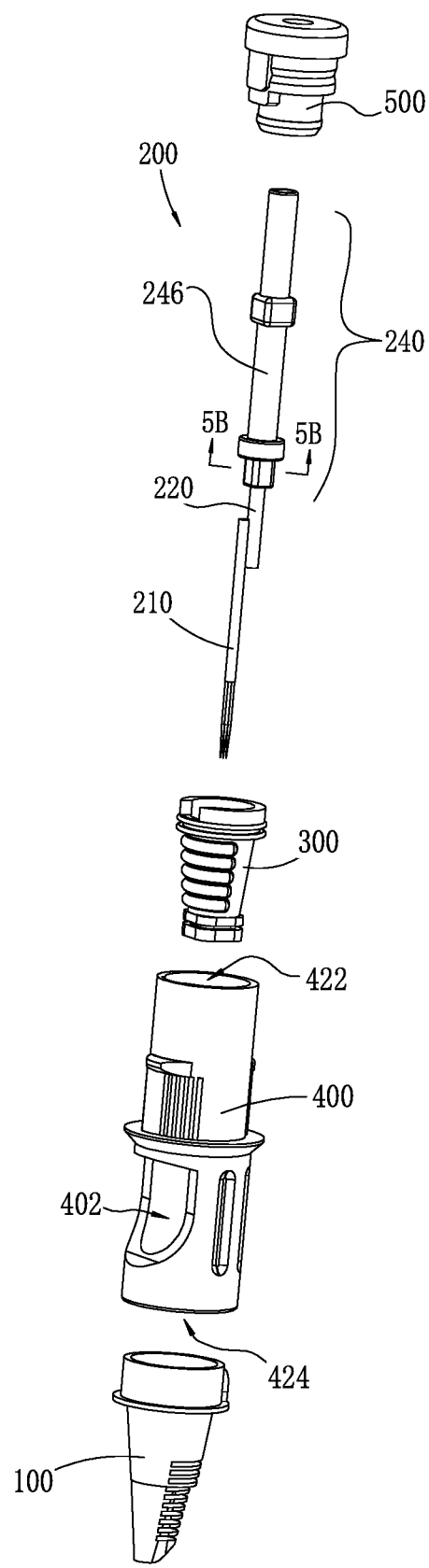
FIG. 2B is an exploded perspective view of the needle module of FIG. 2A.
Figure 2C:
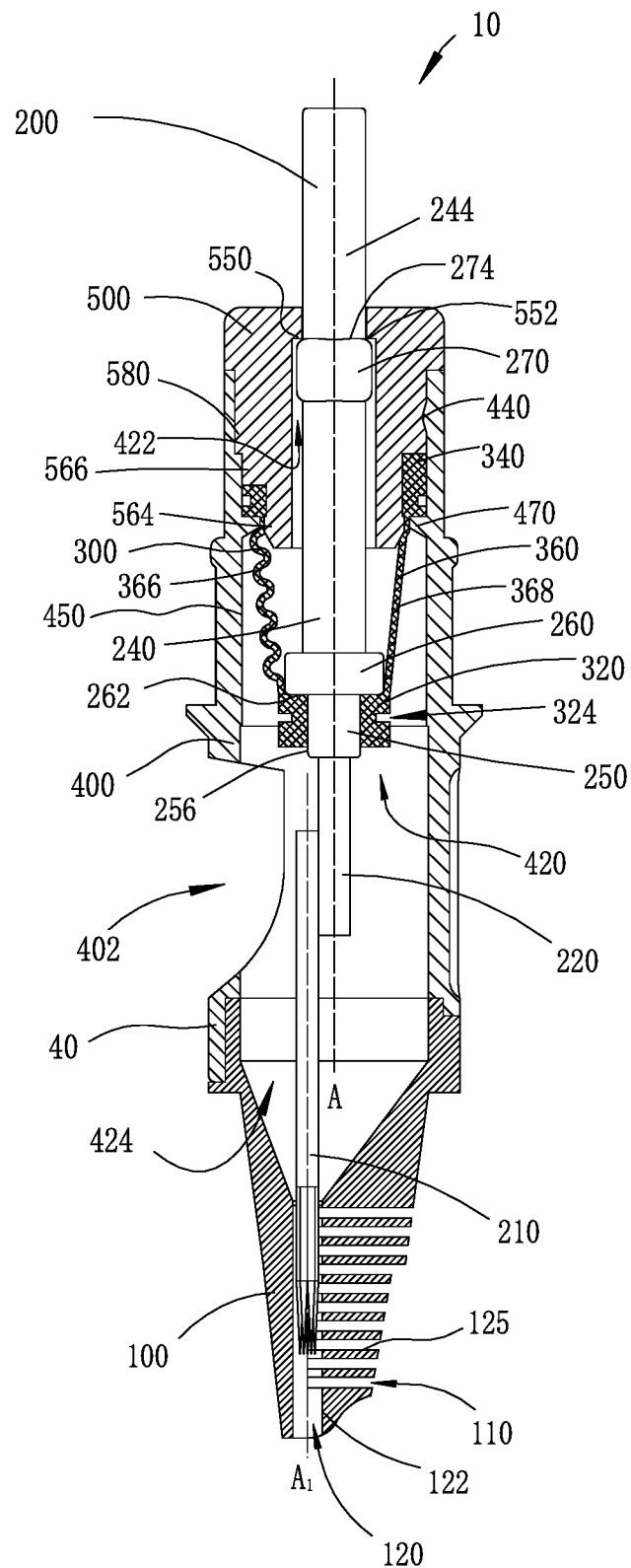
FIG. 2C is a side cross-sectional view of the needle module of FIG. 2A while the needle bundle of the needle module is in a retracted position.

As depicted in FIGS. 2A-2C, the needle module 10 includes a needle housing 40 for movably mounting the needle bundle 200 therein. The needle housing 40 includes a tubular body portion 400, a mouthpiece 100 and a cap 500. The body portion 400 has a tubular longitudinal channel 420 therein for receiving and housing the needle bundle 200. The channel 420 extends from an upper open end 422 to a lower open end 424 of the body portion 400. A mouthpiece 100 with an opening 120 is attached to the lower end 424 of the body portion 400 and a cap 500 is provided at the upper end 422 of the tubular body portion 400. Channel 420 has a longitudinal central axis denoted as axis A in the figures.

The mouthpiece 100 has a needle-guiding wall 122 providing a guide surface for guiding movement of the needle tip portion 210 and feeding ink to the needles, as will be further detailed below. The opening 120 in the mouthpiece 100 has a longitudinal axis denoted as axis $A_1$ in the figures.

To facilitate the reciprocal movement of the needle bundle 200, a biasing member 300 is provided within housing 40 and configured to pull the needle bundle 200 up during each movement cycle after the needle bundle 200 is pushed down by an actuating or driving mechanism such as drive shaft 35.

The biasing member 300 is also configured to bias the tip portion 210 of the needle bundle 200 laterally towards the needle guiding 122, in order to increase or maintain the contact between the needle bundle 200 and the guide surface 122 of the mouth piece 100.

Furthermore, biasing member 300 is configured and assembled to provide a fluid seal between the lower open end 424 and the upper open end 422 of the body portion 400. The biasing member 300 may thus form a diaphragm seal between the lower open end 424 and upper open end 422 of body portion 400.

Upper end portion 340 of biasing member 300 is configured to engage the inner wall 450 of body portion 400. Cap 500 is configured to engage the upper end portion 340 of biasing member 300. The upper end portion 340 is securely retained between cap 500 and tubular body portion 400 and is sealingly affixed to housing 40.

Lower end portion 320 of biasing member 300 is configured to sealingly engage the needle shaft 240 of needle bundle 200.

Biasing member 300 may be formed of a silicone material or another resilient material such as latex, rubber or an elastomer. The resilient material may be selected such that it is sufficiently elastic to be extended under stress to the desired extended position to expose the needle tips, but also sufficiently resilient to provide the required biasing force for returning the needle bundle 200 from the extended position back to the retracted position. In one embodiment, biasing member 300 may be formed from a silicone material with a Shore hardness from about 30 A to about 50 A.

As better seen in FIGS. 4A-4H, the biasing member 300 includes an upper end portion 340, a lower end portion 320, and a tubular section 360 connecting the upper end portion 340 and lower end portion 320.

The upper portion 340 of biasing member 300 is sized and shaped to close fit with the inner wall of tubular body portion 400. The upper portion 340 has two annular ridges 342 and 344 running along the circumference of the outer wall 354 of upper portion 340. The inner wall 352 of upper portion 340 defines an opening 350. The opening 350 is configured to engage the lower segment 560 of cap 500. A keyway 348 is formed in upper portion 340, which may have a crenel shape sized and configured to receive and engage the key profile 566 of cap 500.

The lower portion 320 of biasing member 300 has an opening or keyhole 322 configured to receive and engage key profile 250 of needle bundle 240. The opening 322 is sized and shaped such that key profile 250 fits closely within opening 322 to form a fluid-tight seal between the biasing member 300 and the shaft 240, and the shaft 240 can axially move up and down during operation without breaking the seal.

Upper portion 340 and lower portion 320 are connected by an elastic tubular section 360. The tubular section 360 has a first side 368 and a second, opposite side 366. When properly assembled, the first side 368 is on the same side as the needle guiding surface 122 or faces the needle guiding surface 122, and the second side 366 faces the window 402 and away from the needle guiding surface 122. The tubular section 360 has an axial channel 370, configured to allow the shaft 240 to extend through the axial channel 370.

Upper portion 340 and lower portion 320 each have wall thickness greater than the wall thickness of either first side 368 or second side 366, and are thus more rigid than tubular section 360.

Figure 4A:
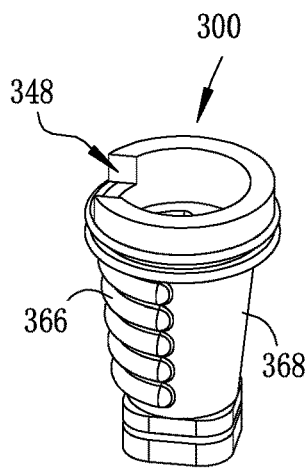
FIGS. 4A and 4B are perspective views of the biasing member in the needle module of FIG. 2.
Figure 4B:
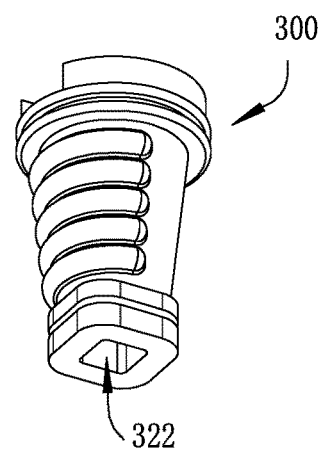
Figure 4C:
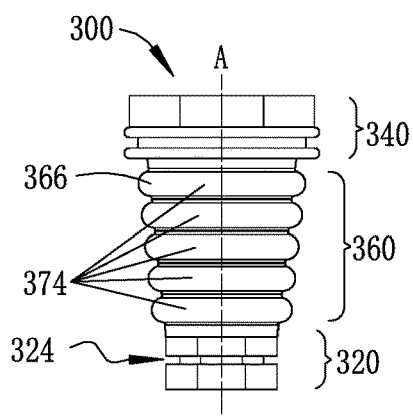
FIG. 4C is a front elevation views of the biasing member of FIGS. 4A and 4B.
Figure 4D:
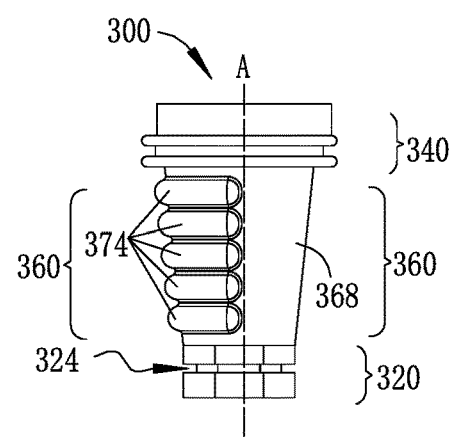
FIG. 4D is a side elevation views of the biasing member of FIGS. 4A and 4B.
Figure 4E:
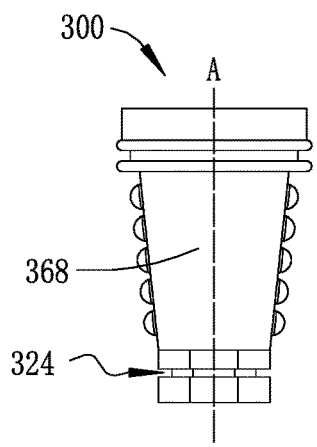
FIG. 4E is a back elevation views of the biasing member of FIGS. 4A and 4B.
Figure 4F:
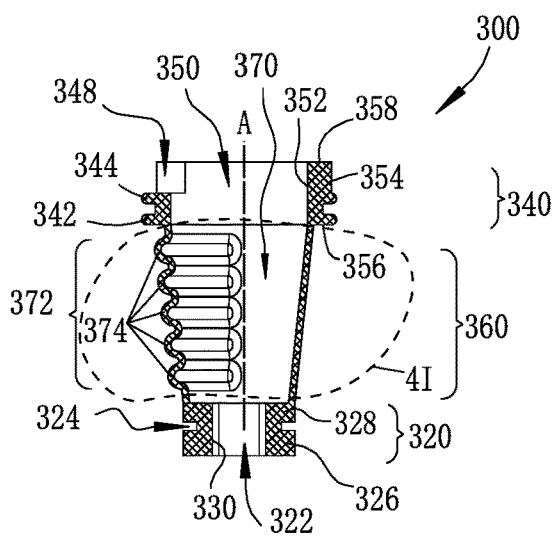
FIG. 4F is a side cross-sectional view of the biasing member of FIGS. 4A and 4B.
Figure 4G:
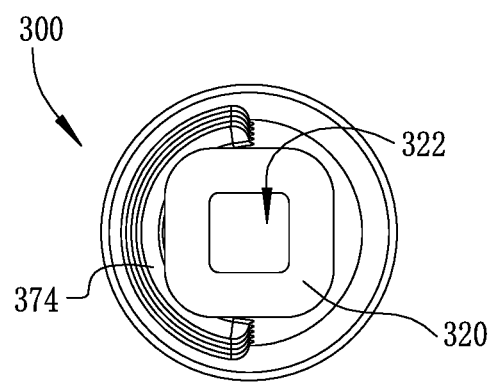
FIG. 4G is a bottom plan view of the biasing member of FIGS. 4A and 4B.
Figure 4H:
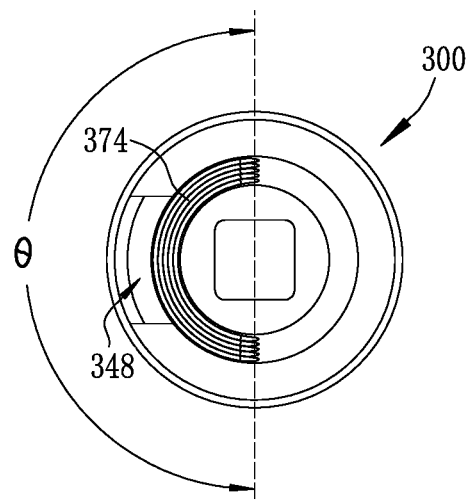
FIG. 4H is a top plan view of the biasing member of FIGS. 4A and 4B.
Figure 4I:
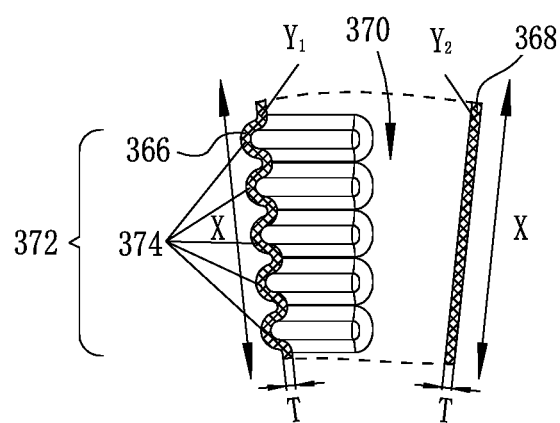
FIG. 4I is an enlarged view of the portion 4I of the biasing member of FIG. 4F.

FIG. 4I illustrates an embodiment of the tubular section 360 of the biasing member 300 in a relaxed state.

As depicted in FIG. 4I, the wall on the second side 366 is curved along the axial direction, and wall on the first side 368 is generally straight (linear) along the axial direction, so that the walls on sides 366 and 368 have different rectified lengths.

As can be appreciated by skilled persons in the art, for a curved line, its rectified length refers to the length of the curve that has been rectified. When rectified, the curve gives a straight line segment with the same length as the curve's arc length. For a straight line, its rectified length is the same as the length of the straight line.

In embodiments disclosed herein, the first side 368 has a shorter rectified length than the second side 366 so that the first side 368 is tensioned more than the second side when the tubular section 360 is stretched due to downward movement of the needle bundle 200.

As illustrated in the figures, the second side 366 may have an arc length or rectified length Y1 and the first side 368 may have a rectified length Y2.

In an embodiment, the second side 366 and the first side 368 of tubular section 360 may each have a thickness T and a length X when the biasing member 300 is in a relaxed state, which may be different from the state in which the needle bundle 200 is at the retracted position. In some embodiments, both first side 368 and the second side 366 may be formed of the same material and have the same or similar wall thickness. Alternatively, first side 368 and second side 366 may have different wall thicknesses. Regardless, as the two sides are curved differently and have different rectified lengths, the first side 368 may nevertheless have a greater stiffness than the second side 366.

The rectified lengths of the sides 366 and 368 in the extended position may be different or may be the same. That is, the second side 366 may be straightened when the tubular section 360 is stretched. However, even after the tubular section 360 has been stretched and the second side 366 has been straightened due to such stretch, the tensions in the two sides 366 and 368 may still be different as the first side 368 is stretched more and thus experiences greater tension than the second side 366.

In a particular embodiment, while the biasing member 300 is in a relaxed state, second side 366 of biasing member 300 may include a corrugated segment 372. As depicted in FIGS. 4A-4F, the corrugated segment 372 may contain five corrugations 374 extending transversely along a portion of the second side 366. As will be appreciated, in other embodiments, the second side 366 may be configured to include any number of corrugations, folds, curves, wrinkles or the like to increase its arc length Y1.

In the embodiment depicted in FIG. 4I, the length Y2 is substantially identical to the length X when the biasing member 300 is in a relaxed state. In different embodiments, the length Y2 may be greater than length X.

Figure 3A:
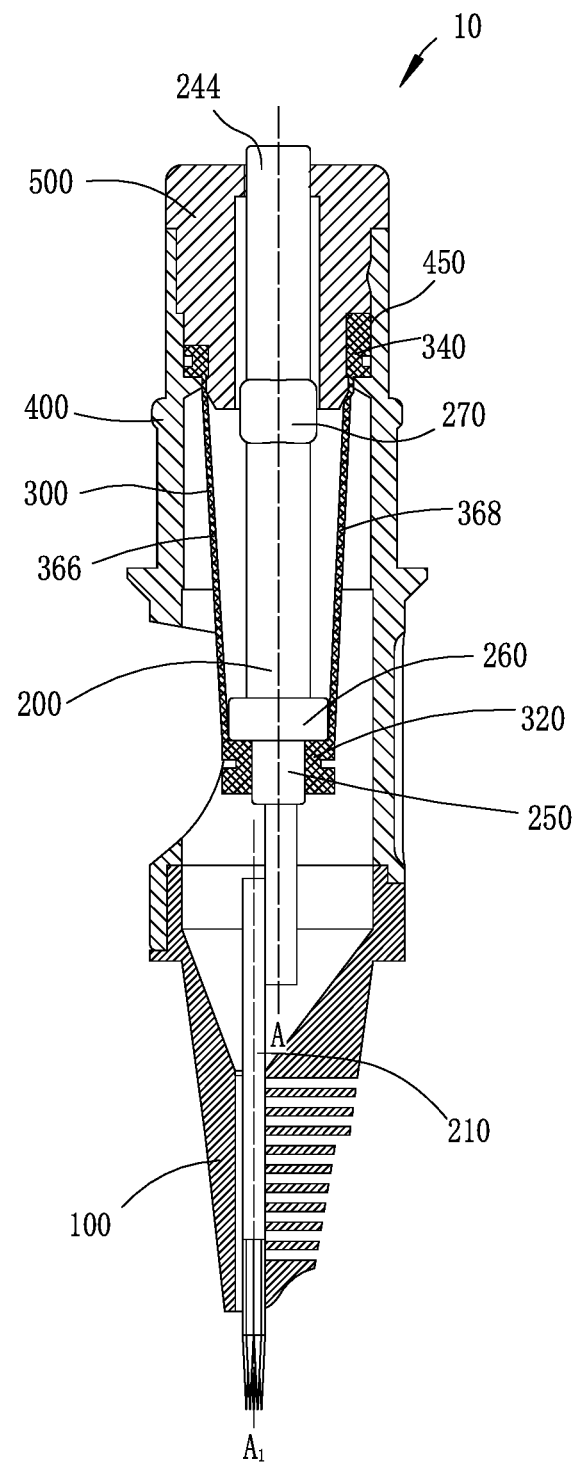
FIG. 3A is a side cross-sectional view of the needle module of FIG. 2A while the needle bundle of the needle module is in an extended position.

The corrugations 374 of corrugated segment 372 on second side 366 spans circumferentially an angle θ about the axial direction of biasing member 300 (axis A in FIG. 3A). In a particular embodiment, θ may be about 180°. In different embodiments θ may vary from about 90° to about 270°.

In a particular embodiment, the corrugated segment 372 may extends over the entire longitudinal length of the second side 366. In alternative embodiments, second side 366 may include both corrugated segments and straight segments.

The second side 366 may be curved in other ways, instead of corrugations, to increase its rectified length and reduce tension when stretched.

Returning to FIG. 2A-2C, the biasing member 300 is configured to engage needle bundle 200 to facilitate the reciprocal movement of needle bundle 200. Needle bundle 200 includes a tip portion 210, a needle shaft portion 220, and a shaft 240.

Tip portion 210 may include one or more needle tips, which may be welded together, or otherwise bounded together. The needle tips may be formed of stainless steel or any other suitable material. The individual needle tip may have any suitable or known needle tip shape. The needle tips may be arranged to form a tip portion that has a generally or substantially cylindrical or conical profile. Alternatively, the needle tips may be arranged side-by-side to form a tip portion that has a generally flattened or band-shaped profile. Rows of side-by-side needles may also be stacked. Such different arrangements of tattoo needles are known in the art and may be referred to as "Round Liner" needles, "Round Shader" needles, "Flat" Needles, or "Magnum" needles, respectively. Tip portion 210 may include 1-18 individual needle tips for "Round Liner" needles and "Round Shader" needles, or may include 4-27 needle tips for "Flat" needles and "Magnum" needles.

As can be appreciated, the cross-sectional sizes or diameters of the needles or needle bundles will affect how the ink will flow. Typically, the smaller the needle tip size or narrower the diameter of the needle tip, the finer and more controlled the stream of ink that flows off each needle tip. Typically, the needle tips in the same needle bundle may be of the same or similar sizes. The size of the needle tips may be selected based on the desired effects by the operator or user. Different sizes may be used for different reasons. Standard sizes of needles may be used. The diameters of the individual needles may be 0.25 mm, 0.30 mm, or 0.35 mm in some embodiments. The designs of the needle tips may be selected and vary as known in the art based on the desired tattooing techniques and purposes to be applied.

The number of needles in a needle bundle may vary from 1 to 27 or more as desired. For example, commercially available round needle bundles typically have 1, 3, 5, 7, 8, 9, 11, 14, or 18 needles in each bundle. It would also be appreciated that the overall profile of the needle bundle may change and vary depending on the number of needles in the bundle, their arrangement, the amount of soldering material used, or other factors.

The welded needle tips in tip portion 210 are supported on needle shaft portion 220. The axis of needle shaft portion 220 is axially aligned with the axis of shaft 240 (axis A in FIG. 2C), but is off-set from the axis of the tip portion 210 (axis A1 in FIG. 2C). The needle shaft portion 220 may be formed of stainless steel or another suitable material. It should be sufficiently rigid and strong to support stable movement of the needle tip portion 210 during operation. Tip portion 210 may be welded onto needle shaft portion 220.

Needle shaft portion 220 is coupled with shaft 240 for driving the tip portion 210. With reference to also FIGS. 5A and 5B, the shaft 240 may have a bore 248 at the lower end 242 for receiving an upper end of shaft portion 220. The needle shaft portion 220 and shaft 240 may be engaged and locked in any suitable manner. The bore 248 at the lower end 242 of shaft 240 may be cylindrical or have another cross-sectional shape. Needle shaft portion 220 may be inserted into the bore 248 and may be attached to the wall of the bore of the shaft 240 with an adhesive, such as glue.

Shaft 240 may be formed of a plastic material or another suitable material for transmitting the axial driving force to needle shaft portion 220 and then indirectly to tip portion 210.

As better illustrated in FIG. 2C, shaft 240 passes through the biasing member 300 and is sealingly coupled to the central opening 322 of the biasing member 300 (see FIGS. 4A-4H). Shaft 240 has a key profile 250 at the lower end 242 of the shaft 240 for engaging the keyhole defined by the central opening 322 of the biasing member 300 to lock the orientation of the shaft 240 and shaft portion 220 with respect to the biasing member 300. In a particular embodiment, the central opening 322 and key profile 250 have corresponding rectangular or square cross-sections. The sizes of the keyhole defined by the central opening 322 and the key profile 250 are matched so the shaft 240 can sealingly engage the biasing member 300 to prevent leakage of ink through any gap between the central opening 322 and key profile 250.

The shaft 240 includes a stopper 260 immediately above the key profile 250, and the lower surface of the stopper 260 forms a key shoulder 262, which is larger in size than the central opening 322 of the biasing member, so that the lower end portion 320 of the biasing member 300 abuts the key shoulder 262 and biases the shaft 240 towards the upper end 422 of the tubular body portion 400.

An enlarged stopper section 270 is located near the upper end 244 of the body 246 of the shaft 240, which has an enlarged axial cross-section as compared to other body portions of the shaft 240. The size of the stopper section 270 is larger than the upper channel 540 of the cap 500 so that it can function as a stopper to limit the upward movement of the shaft 240.

As illustrated in FIGS. 2A-2C, the needle bundle 200 is mounted within a needle housing 40. The needle housing 40 includes cap 500, tubular body portion 400 and mouthpiece 100.

With reference to FIGS. 6A-6D, the cap 500 includes three segments, a lower segment 560, a middle segment 570, and an upper segment 590. The outer diameter of upper segment 590 is greater than the outer diameter of the middle segment 570, and the outer diameter of the middle segment is greater than the outer diameter of the lower segment 560.

The middle segment 570 of cap 500 has a key profile 580, for engaging the keyway 430 on the inner wall 450 of the body portion 400. Cap 500 also has an annular groove 582 extending around the outer circumference of middle segment 570, except where it is interrupted by key profile 580. The groove 582 is positioned and sized to engage ridges 440 on the inner wall 450 of the body portion 400.

The lower segment 560 of cap 500 has another key profile 566, which is sized and configured to engage the keyway 348 in the upper portion 340 of biasing member 300. Key profile 566 may be sized so that it is flush with outer diameter of the middle segment 570 of cap 500. The lower segment 560 has a raised annular rim 564 towards its lower end. As will be explained in greater detail below, when the lower segment 560 of cap 500 is inserted into opening 350 of the upper end portion 340 of biasing member 300, the annular rim 564 abuts the upper portion 340 of biasing member 300 to prevent downward movement of biasing member 300 during reciprocating movement of the needle bundle 200. The lower segment 560 also has a tapered edge 568 at its lower end. The tapered edge 568 allows easier insertion of the cap 500 into the opening 350 of the biasing member 300.

Cap 500 has a central axial channel 520 to allow the shaft 240 to pass through and axially move therethrough during operation.

Channel 520 has a lower channel 530 and an upper channel 540. The lower channel 530 and the upper channel 540 are sized differently so that the lower channel 530 and the upper channel 540 form a shoulder 550. When the needle bundle 200 is in a retracted state and before needle module 10 is incorporated into tattooing device 60, the upper surface 274 of the stopper section 270 on the needle bundle 200 abuts the lower surface 552 of shoulder 550 to limit further upward movement of the needle bundle 200.

Figure 5A:
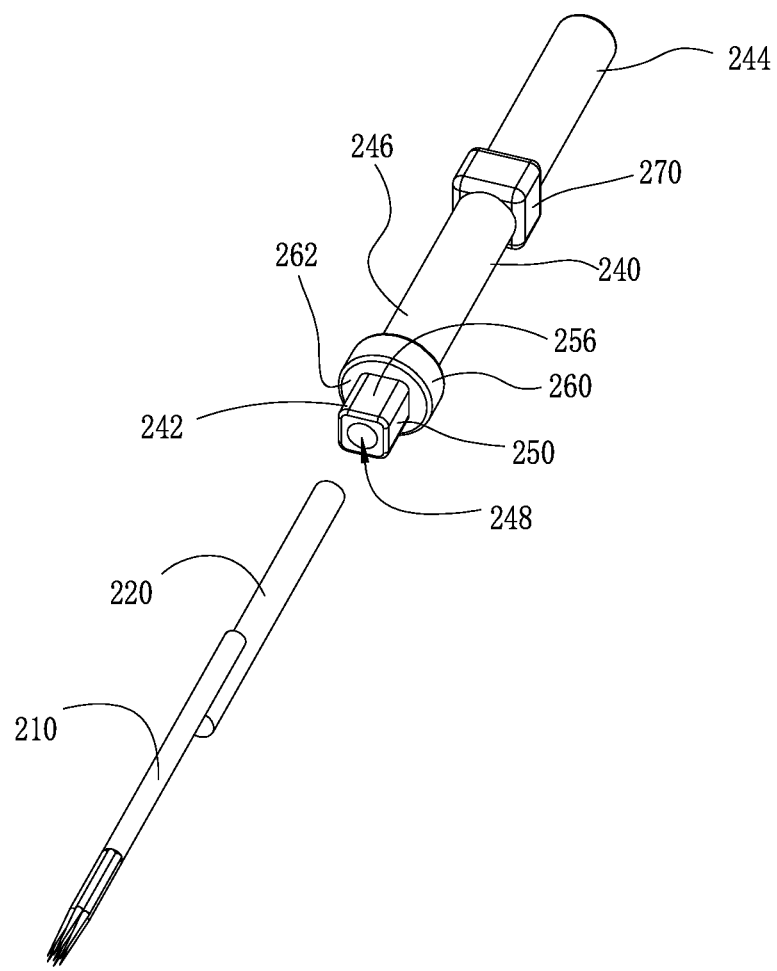
FIG. 5A is an exploded perspective view of the needle bundle in the needle module of FIGS. 2A-2C.
Figure 5B:
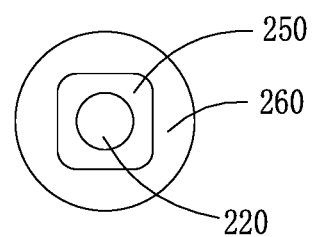
FIG. 5B is an axially cross-sectional view of the needle bundle, taken along line 5B-5B in FIG. 2B.
Figure 6A:
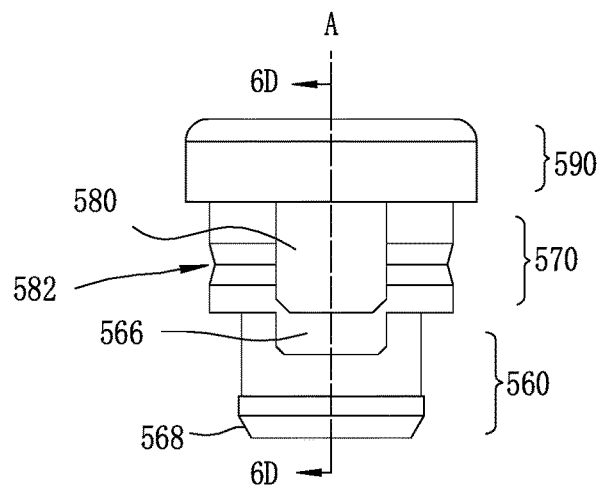
FIG. 6A is a front elevation view of the cap in the needle module of FIGS. 2A-2C.
Figure 6B:
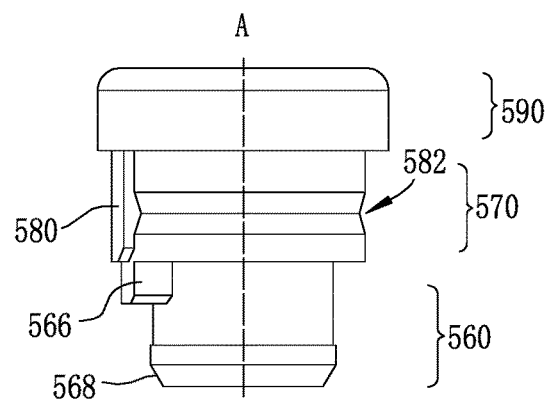
FIG. 6B is a right side elevation view of the cap.
Figure 6C:
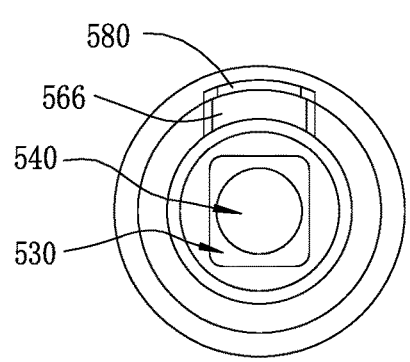
FIG. 6C is a bottom view of the cap.
Figure 6D:
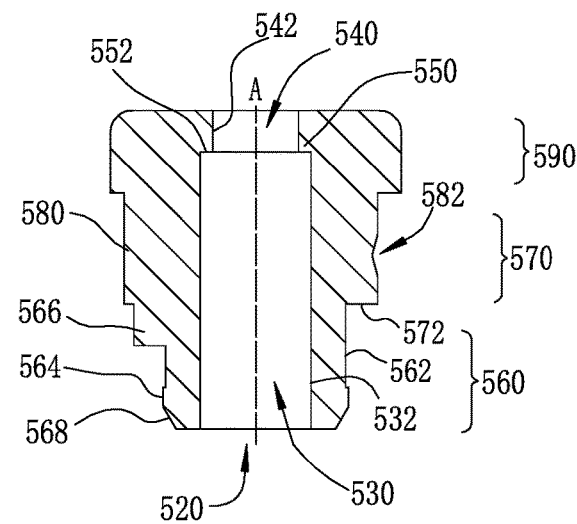
FIG. 6D is a right side cross-sectional view of the cap along the central axis of the cap, taken along line 6D-6D in FIG. 6A.
Figure 7A:
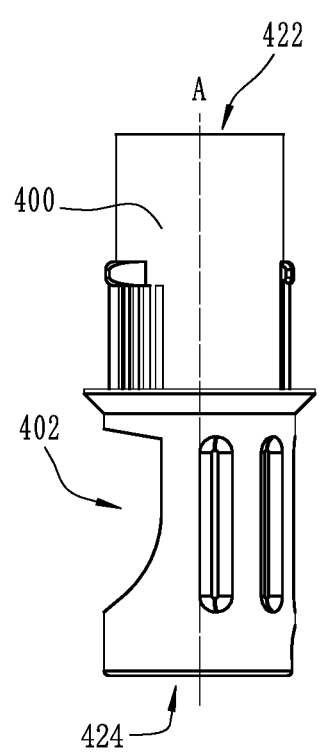
FIG. 7A is a side elevation view of the body portion of the needle module of FIGS. 2A-2C.
Figure 7B:
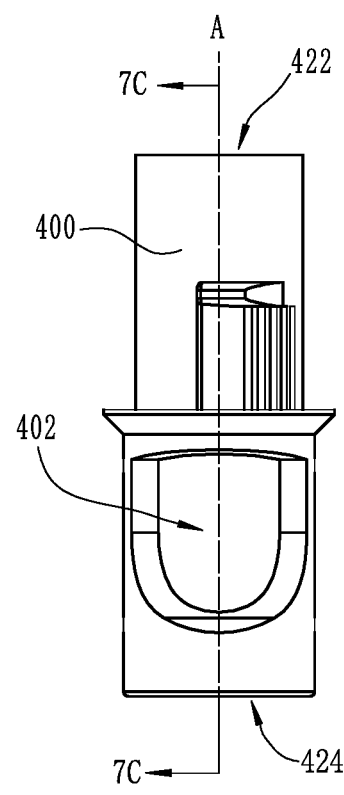
FIG. 7B is a front elevation view of the body portion.
Figure 7C:
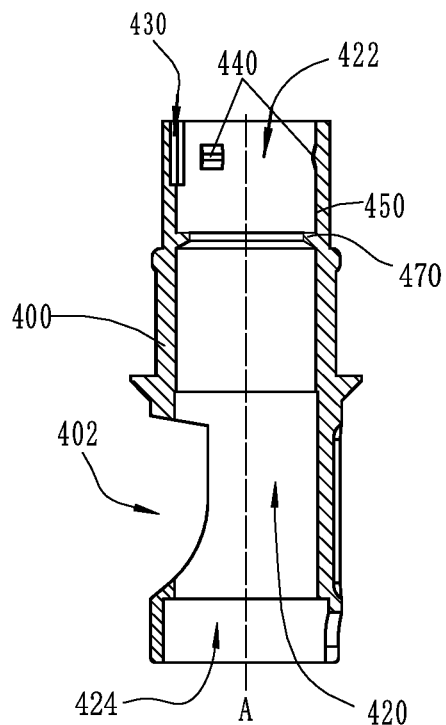
FIG. 7C is a side cross-sectional view of the body portion, taken along line 7C-7C in FIG. 7B.
Figure 7D:
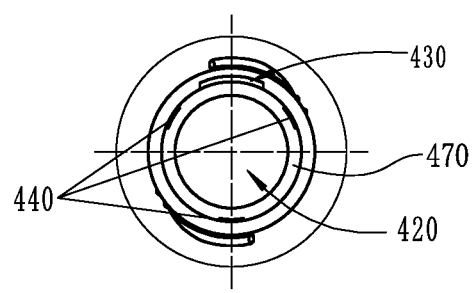
FIG. 7D is a top plan view of the body portion.
Figures 8A, 8B:
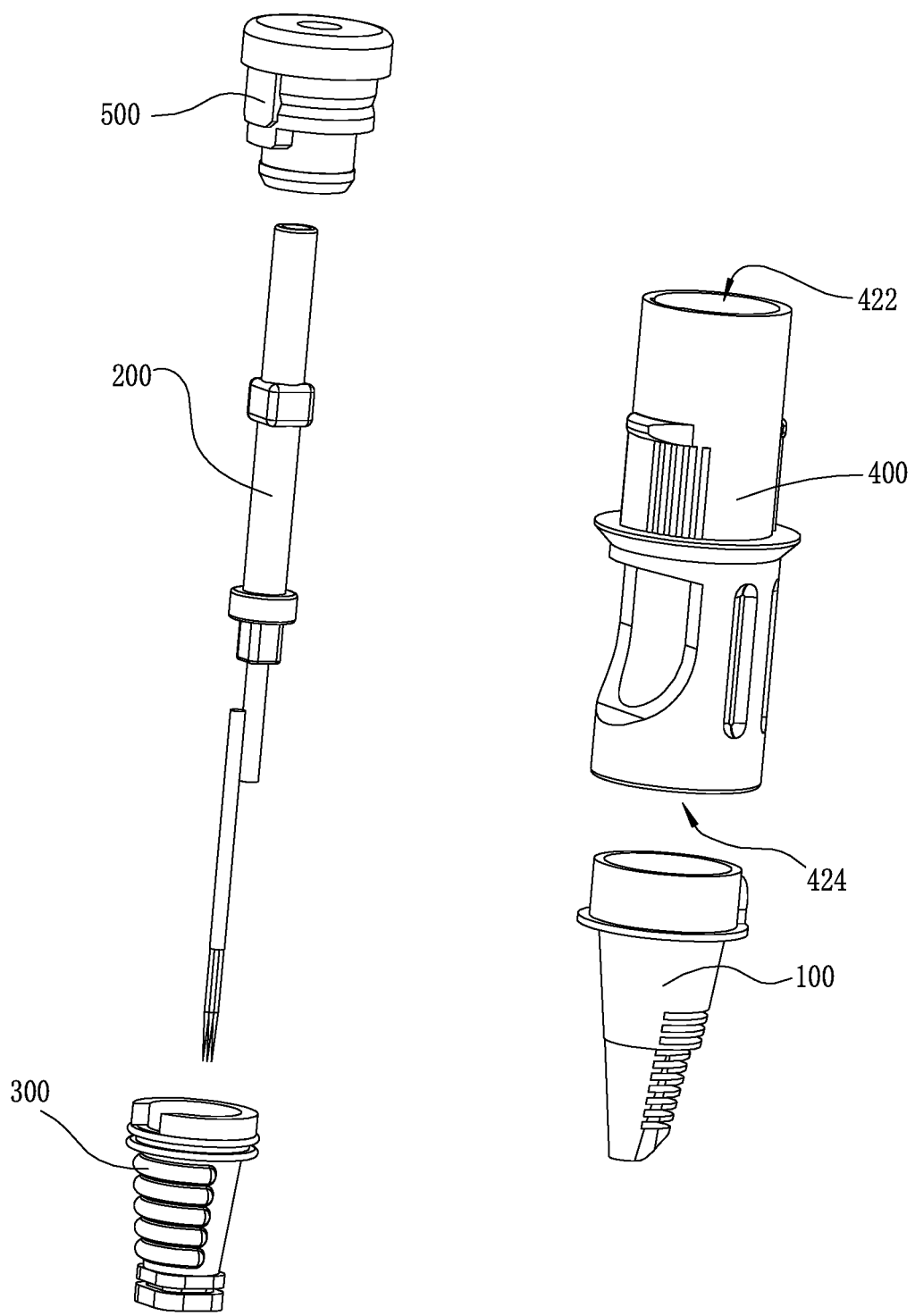
FIG. 8A is a perspective view illustrating the spatial relationship and assembly of the cap, needle bundle and biasing member of the needle module.
FIG. 8B is a perspective view illustrating the spatial relationship and assembly of the housing and mouthpiece of the needle module.
Figures 8C, 8D:
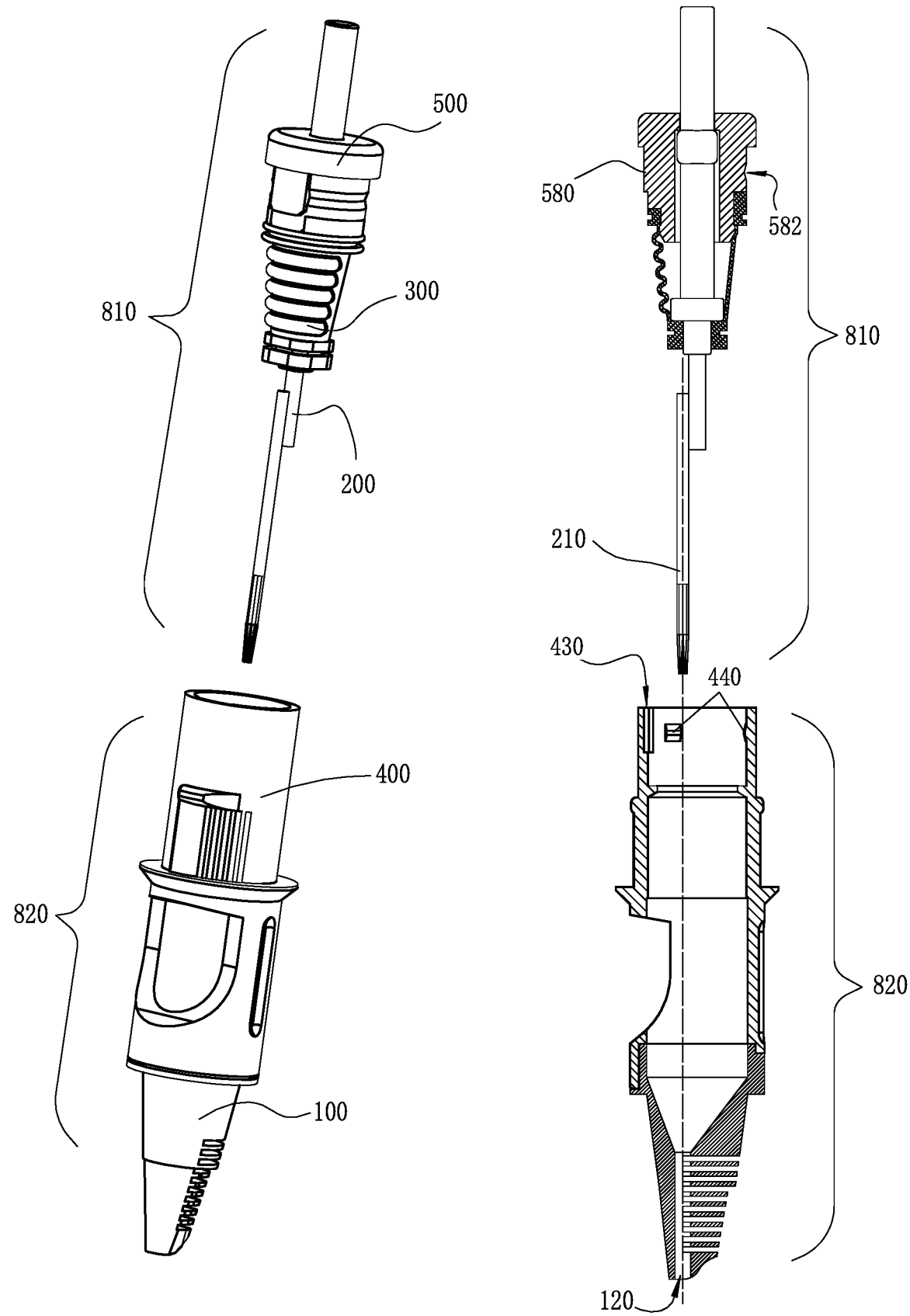
FIG. 8C is a perspective view illustrating the spatial relationship and assembly of the inner assembly shown in FIG. 8A and the outer assembly shown in FIG. 8B to form the needle module.
FIG. 8D is a cross-sectional view thereof.

The lower channel 530 of channel 520 has a substantially constant cross-sectional profile along its length. The inner dimensions of lower channel 530 are sized to be larger than the outer dimensions of stopper section 270, and there may be a gap between the stopper 270 and the inner wall 532 that defines lower channel 530 when the stopper 270 is inserted into channel 530. Such a gap may allow smooth movement of the needle bundle 200 and shaft 240 in the housing 40, reducing or preventing the risk of jamming or too much friction. Lower channel 530 and stopper 270 are shaped and configured to prevent rotation of needle bundle 200 about its longitudinal axis (Axis A in FIG. 2C) during operation of needle module 10. More particularly, lower channel 530 and stopper 270 may have non-circular cross-sections such that stopper 270 cannot freely rotate about its longitudinal axis (Axis A in FIG. 2C) inside lower channel 530. As depicted in FIGS. 5A, 5B and 6C, lower channel 530 and stopper 270 may each have a square-shaped cross-section. The profile of the cross-sections of channel 530 and stopper 270 may also be, for example, polygonal, oval, or irregularly shaped. Channel 530 and stopper 270 may have similar or matching cross-sectional shapes.

In an embodiment, upper channel 540 and the shaft bodies may be generally cylindrical in shape, and the inner diameter of the upper channel 540 may be sized to be larger than the outer diameter of the body 246 of shaft 240 but smaller than an outer dimension of stopper 270. These parts may be sized so that a gap is provided between the shaft 240 and the inner wall 542 that defines upper channel 540. Such a gap may allow smooth movement of the needle bundle 200 and shaft 240 in the housing 40, reducing or preventing the risk of jamming or too much friction.

Cap 500 may be made of a plastic material, or any other suitable material.

As illustrated in FIGS. 2A-2C, cap 500 is connected and engaged with the upper open end 422 of tubular body portion 400. Body portion 400 has a tubular longitudinal channel therein for receiving and housing needle bundle 200. The channel 420 extends from an upper open end 422 to a lower open end 424 of the body portion 400. Channel 420 has a longitudinal central axis denoted as axis A in the figures. Body portion 400 also has an observation window 402 for observing the state and operation of the needle bundle 200

Body portion 400 may be made of a plastic material, or any other suitable material.

With reference to FIGS. 7A-7D, an internal annular ledge 470 extends along the circumference of the inner wall 450 of body portion 400 near the upper open end 422. Annular ledge 470 abuts the lower surface 356 of upper portion 340 of biasing member 300 (see FIGS. 4A-4H) to prevent downward movement of biasing member 300 during reciprocating movement of the needle bundle 200. There are also three ridges 440 positioned equidistant from one another along the circumference of the inner wall 450 of body portion 400 near the upper open end 422 for engaging a corresponding groove 582 in the cap 500.

The upper open end 422 of the body portion 400 also has a keyway 430 for engaging a key profile 580 of the cap 500 and orienting the cap 500.

As illustrated in FIGS. 2A-2C, at its lower open end 424, body portion 400 is connected and engaged with mouthpiece 100.

The detailed construction and mechanism for the mouthpiece are not the focus of this disclosure and can be implemented by a skilled person in the art according to known techniques or constructions, except in aspects specifically described below. Thus, some of these details will not be discussed herein.

In an embodiment, mouthpiece 100 may be constructed and operated as disclosed in U.S. patent application Ser. No. 15/874,597 by Xiao, the entire contents of which are incorporated herein by reference.

The mouthpiece 100 is configured to support and allow axial movement of the tip portion 210 through an opening 120 in the mouthpiece 100. The mouthpiece 100 may be made of a plastic material or another suitable material. The opening 120 may have a shape configured to match the profile of the tip portion 210 of needle bundle 200. For example, for round or circular tip portion 210, the opening 120 may have a circular or diamond shape; for flat tip portion 210, the opening 120 may have a rectangular shape. The size of opening 120 is also selected to accommodate the size of the tip portion 210. To avoid jamming during use and to accommodate different needle sizes or needle bundle sizes, the size of the opening 120 of the mouthpiece 100 may be selected to allow some play of the needle bundle to be used. That is, the size of opening 120 is slightly larger than the size of the needle tip portion 210, so that there is a gap between the inner wall of opening 120 and the needle tip portion 210 on the opposite side of the guide surface 122. This gap allows smooth movement of the needle tip and size variations of the tip portion 210, without jamming.

Even though there is a gap between the needle tip portion 210 and the opening 120, the risk that the tip portion 210 will vibrate sideways is low as the tip portion 210 is biased against the guide surface 122, which provides a stable support surface for the movement of the needle tip. In other words, even when the size of the opening 120 is relatively large, and there is a gap between the tip portion 210 of the needle bundle 200 and the inner surfaces of the mouthpiece 100, tip portion 210 will be biased to contact and abut against the guide surface 122, and maintain the contact during reciprocal movement of the needle bundle 200.

Mouthpiece 100 is also configured to function as an ink feeding device. Specifically, as illustrated in FIGS. 2A-2C, ink storage grooves 110 defined by groove walls 125 are provided on guide surface 122, for storing ink. Each groove 110 extends generally transversely in relation to the axial direction and the direction of movement of the needle bundle 200. Groove walls 125 and grooves 110 may be generally parallel to one another, and are located near, but above, the lower open end of mouthpiece 100. Grooves 110 may extend radially to the external surface of the mouthpiece 100 to allow easy filling of ink during use. That is, each groove 110 may be open to the external surface of mouthpiece 100 as depicted in these figures. Each individual groove 110 is formed between two opposing groove walls 125 having a thin gap between the opposing groove walls 125 such that when the mouthpiece 100 is brought into contact with an ink source (such as when it is dipped in an ink bottle), ink can be sucked into and fill the gap due to capillary action. The ink in the gap can be normally retained in place due to surface tension and adhesion of the ink liquid to the groove walls 125.

When the tip portion 210 of the needle bundle 200 moves downward across the grooves 110 while being pressed against the guide surface 122, the moving needles will contact the liquid surface of the ink stored in the grooves 110 and bring ink out of grooves 110, and then carry the ink with the needles or allow the ink to flow along the needles and be applied to the skin.

As depicted in FIGS. 2A-2C and 8A-8D, biasing member 300, needle bundle 200, cap 500, body portion 400 and mouthpiece 100 are assembled together to form a needle module 10.

An inner assembly 810 of needle module 10 is assembled from needle bundle 200, the biasing member 300, and the cap 500.

The needle bundle 200 is inserted into biasing member 300 such that stopper 260 abuts lower portion 320 of biasing member 300. The key profile 250 is snugly retained within the opening 322 of biasing member 300 such that a fluid-tight seal is created between the needle bundle 200 and lower portion 320 of biasing member 300. In alternative embodiments, needle bundle 200 may be retained within, and attached to, opening 322 in another manner. For example, in one alternative embodiment, needle bundle 200 may be attached to opening 322 by an adhesive, such as glue. In another alternative embodiment, a resilient band, such as an O-ring, may encircle the outer circumference of lower portion 320 and urge lower portion 320 against needle bundle 200.

Cap 500 is coupled to the biasing member 300 such that the lower segment of 560 of cap 500 is snugly retained within the opening 350 defined by the inner wall 352 of upper portion 340. The upper surface 358 of biasing member 300 may abut the lower surface 572 of middle segment 570 of cap 500 when lower segment 560 of cap 500 is inserted into opening 350 of biasing member 300. Upper portion 340 of biasing member 300 encircles lower segment 560 of cap 500, and is longitudinally secured in place between middle segment 570 of cap 500 and annular rim 564. Key profile 566 of cap 500 is inserted into keyway 348 in the upper portion 340 of biasing member 300.

The axes of biasing member 300 and cap 500 are aligned with the axis of shaft 240 (axis A in FIG. 2C). Biasing member 300, cap 500 and needle bundle 200, are configured and oriented during assembly such that first side 368 of biasing member 300 is positioned axially opposite of tip portion 210.

Mouthpiece 100 may be assembled with body portion 400 to create an outer assembly 820 of needle module 10. Mouthpiece 100 may be connected and engaged with the lower open end 424 of body portion 400 in any suitable manner, with any suitable engagement or locking mechanism. For example, these parts may be engaged by tabs, threads, clamps, pins, keys, and corresponding openings, notches, threads, holes, keyways, or the like as can be understood by those skilled in the art. As depicted, mouthpiece 100 may frictionally engage the inner walls of body portion 400, and may be interlocked in the mounted positions with a tab. Mouthpiece 100 may be attached to body portion 400 by an adhesive, such as glue. In alternative embodiments, mouthpiece 100 may be welded onto body portion 400. In further alternative embodiments, mouthpiece 100 and body portion 400 may be formed in an integral unit.

Inner assembly 810 and outer assembly 820 may be assembled to create needle module 10 as shown in FIGS. 2A-2C and FIGS. 8A-8D.

Inner assembly 810 is inserted into upper open end 422 of body portion 400 such that upper portion 340 of biasing member 300 is retained within the channel 420 defined by inner wall 450 of body portion 400. Upper portion 340 fits snugly within channel 420 between inner wall 450 of body portion 400 and outer wall 562 of lower segment 560. The lower surface 356 of upper portion 340 of biasing member abuts the annular ledge 470 of body portion 400. The annular rim 564 of cap 500 is concentrically aligned with annular ledge 470. The portion of elastic tubular 360 near biasing member 300 is closely wedged between annular rim 564 and annular ledge 470. Together, annular rim 564 of cap 500 and annular ledge 470 of body portion 400 retains upper portion 340 of biasing member 300 such that upper portion 340 does not move in a longitudinal direction during reciprocating movement of needle bundle 200. Ridges 342 and 344 on upper portion 340 of biasing member 300 are configured to abut and resiliently grip the inner wall 450 of body portion 400 and to create a fluid-tight seal between upper portion 340 and body portion 400. In alternative embodiments biasing member 300 may be sealingly attached to body portion 400 in another manner. For example, upper portion 340 may be attached to the inner wall 450 of body portion 400 by an adhesive, such as glue.

Ridges 440 of body portion 400 engage groove 582 of cap 500, thereby allowing body portion 400 to securely retain cap 500. Key profile 580 of cap 500 is inserted into keyway 430 of body portion 400.

Cap 500, needle bundle 200, biasing member 300, body portion 400 and mouthpiece 100 are configured and oriented during assembly such that the axis of the needle tip portion 210 aligns with the axis of opening 120 in mouthpiece 100 (see axis A1 in FIG. 2C).

As illustrated in FIGS. 1A and 1B, the assembled needle assembly 10, handle 20, and base device 30 form an ink applicator 60, or in particular, a tattooing device.

During operation, an operator may hold the ink applicator 60 with handle 20 in her hand, and dip the mouthpiece 100 in an ink container (not shown) to fill the ink storage grooves 110 with the desired ink. The needle actuator is activated to drive the drive shaft 35 and consequently needle shaft 240 and tip portion 210 of the needle bundle 200 downward to an extended position as depicted in FIG. 3A. After each downward stroke, the biasing member 300 is stretched and pulls the tip portion 210 back up to a retracted position once the drive shaft 35 stops the downward movement and moves upward. The upward movement of the needle bundle 200 may continue until drive shaft 35 reaches the end of its upward stroke, at which point drive shaft 35 may cease its upward movement and correspondingly prevent further upward movement of the needle bundle 200. After needle bundle 200 comes to the retracted position, the needle actuator may then re-start the downward drive in the next cycle. This process repeats so as to drive the needle bundle 200 to reciprocally move longitudinally along the axial direction of the shafts 35 and 240. The base device 30 may be configured to operate at a drive frequency of about 80 to 150 Hz. The operator may adjust the operating frequency during operation. In some tattooing machines, the tattoo needles may be operated to puncture the skin from 3000 to 10,000 times per minute. The needles may penetrate the skin and reach a depth of about 1 mm to about 2 mm. The vertical moving distance of the drive shaft 35 is typically about 2 mm to 5 mm, and the needle bundle 200 may similarly move about 2 to 5 mm during each stroke. The vertical moving distance of the drive shaft 35 may be equal to or greater than the vertical moving distance of the needle bundle 200. As depicted in FIG. 2C, the needle tip portion 210 is completely enveloped by mouthpiece 100 when needle bundle 200 is in a retracted state, however, needle tip portion 210 may extend more than about 2 mm to 5 mm beyond opening 120 of mouthpiece 100 and thus needle tip portion 210 need not be housed completely within mouthpiece 100 when needle bundle 200 is in the retracted state.

As the tip portion 210 moves up and down, the operator may bring it to contact a subject's skin to apply ink to the skin, as in a conventional operation, which can be understood by those skilled in the art.

After each operation or use, the needle module 10 may be removed and disposed. The handle 20 may be next removed, and may also be disposed. The operator can take off disposable gloves and clean her hands at this time before touching other parts of the ink applicator 60.

For the next operation, a new needle module and new handle may be connected to the base device 30, and used similarly as described above.

The needle module 10 may be used directly after opening the needle module packaging without further cleaning, sanitization, or sterilization, and can be disposed after a single use without cleaning or any other treatment.

For clarity, it is noted that "single use" may refer to use of a needle or needle module for one complete operation on a single individual subject. During this operation, different needle modules may be used to apply different ink colors or for different purposes. For example, it may be typical to use two to five different types of needles during a single operation on a subject, depending on the complexity of the design to be applied.

With reference to FIGS. 2C and 3A-3D, the operation of the biasing member 300 will now be described in greater detail. For ease of viewing, the mouthpiece 100 and body portion 400 are not shown in FIGS. 3B and 3C.

Figure 3B:
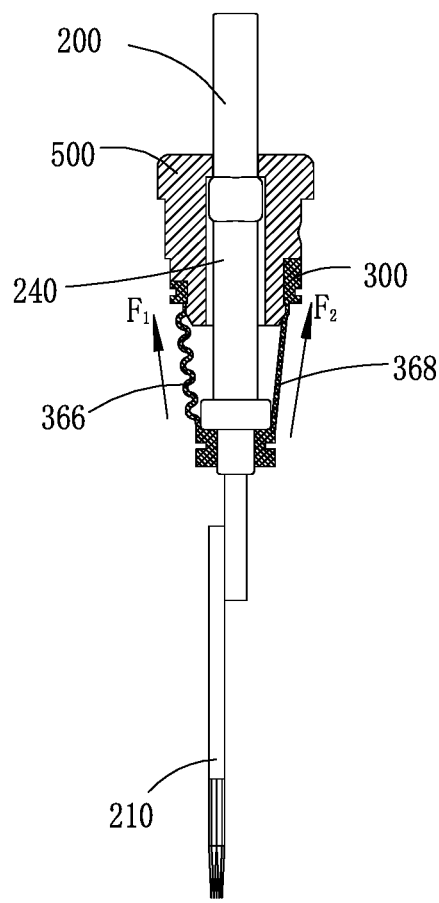
FIG. 3B is a side cross-sectional view of certain parts of the needle module of FIG. 2C.

Biasing member 300 is normally slightly tensioned to bias the needle bundle 200 upward into a retracted state as depicted in FIGS. 2C and 3B. Second side 366 of biasing member 300 applies a force $F_1$ and first side 368 of biasing member 300 applies a force $F_2$, as shown in FIG. 3B. As shown in FIG. 3D, force $F_1$ has an axial component $F_{1A}$ and a radial component $F_{1R}$, and force $F_2$ has axial component $F_{2A}$ and a radial component $F_{2R}$. The total upward biasing force $F_A$ is thus the sum of the axial components $F_{1A}$ and $F_{2A}$, and the total radial biasing force $F_R$ is the difference between the radial components $F_{1R}$ and $F_{2R}$.

As explained above, the biasing member 300 is configured such that the stiffness of first side 368 is greater than the stiffness of second side 366, notwithstanding that second side 366 and first side 368 may be constructed of identical materials and are of identical thickness. For example, second side 366 may be corrugated, curved, folded, wrinkled, or the like so as to reduce its stiffness relative to first side 368. Thus, the magnitude of force $F_1$ is smaller than the magnitude of force $F_2$, the magnitude of axial component $F_{1A}$ is smaller than the magnitude of axial component $F_{2A}$, and the magnitude of radial component $F_{1R}$ is smaller than the magnitude of radial component $F_{2R}$. The total radial biasing force $F_R$ thus applies against the needle bundle 200 and biases the tip portion 210 against guide surface 122. A slight lean of needle bundle 200 off the axial direction of the axis A or $A_1$ would allow the needle portion 210 to contact and be supported by needle guiding wall 122.

Figure 3C:
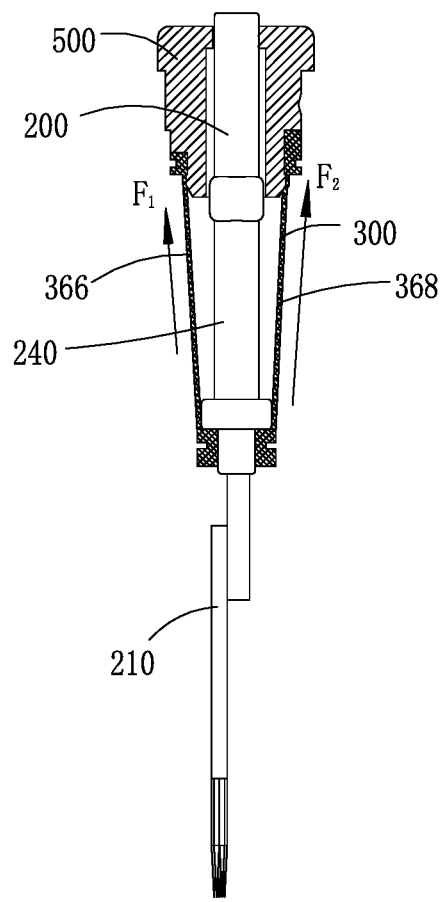
FIG. 3C is a side cross-sectional view of certain parts of the needle module of FIG. 3A.
Figure 3D:
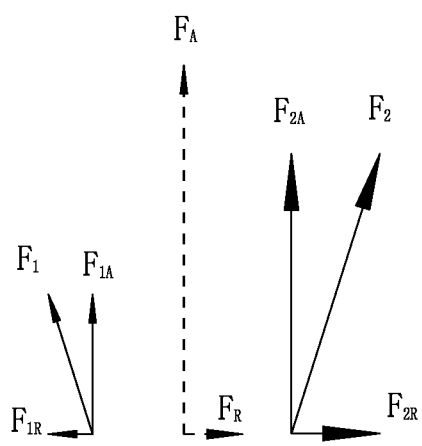
FIG. 3D is a force diagram showing the force applied to the needle bundle shown in FIGS. 3B and 3C.

As depicted in FIGS. 3A and 3C, when the needle bundle 200 is pushed downward by a drive shaft (not shown) through shaft 240, the biasing member 300 is stretched and provides an increased axial biasing force upward (force $F_A$ as illustrated in FIG. 3D). However, the radial force (force $F_R$ as illustrated in FIG. 3D) that biases needle tip portion 210 against guide surface 122 will not change significantly during axial movement of the needle bundle.

Due to the biasing force applied to the biasing member 300 during operation, tubular section 360 may experience considerable strain. To reduce the risk of breakage, the sides of tubing 360 may thus have a minimally acceptable thickness. However, as the thickness of the sides of tubing 360 is increased, more force is required to push needle bundle 200 down into an extended position, and consequently more energy is required to operate the ink applicator 60. A convenient effect of an embodiment disclosed herein is that the relative stiffness of second side 366 and first side 368 may be altered without differing the thickness of second side 366 and second side 368. This allows biasing member 300 to be configured to apply a radial biasing force $F_R$ without compromising the structural integrity of tubular section 360 or increasing the energy usage of ink applicator 60.

As can be appreciated, the biasing member 300 may be configured to provide both the longitudinal biasing force $F_A$ and the radial biasing force $F_R$ (see FIG. 3D) with a simple construction structure. The configuration of biasing member 300 thus obviates the need for separate biasing members to separate provide the longitudinal biasing force $F_A$ and the radial biasing force $F_R$ and simplifies construction of needle module 10.

When the needle bundle 200 pushed downward by a drive shaft 35 (see FIGS. 1A and 1B) through shaft 240, lower portion 320 of biasing member 300 may become stretched and deformed. Groove 324 (also see FIG. 4F) runs through lower portion 320 such that strain experienced by lower portion 320 is isolated in the upper segment 328 of lower portion 320. Deformation of lower segment 326 of lower portion 320 is thus minimized such that the inner surface 330 of lower portion 320 will remain in fluid-tight contact with the outer surface 256 of key profile 250 during longitudinal reciprocating movement of needle bundle 200.

Ridges 342 and 344 of upper end portion 340 resiliently engages the inner wall 450 of body portion 400 such that the upper end portion 340 of biasing member 300 remains in fluid-tight contact with the body portion 400 during longitudinal reciprocal movement of needle bundle 200.

As now can be appreciated, during operation, the biasing member 300 separates the lower open end 424 of body portion 400 from the upper open end 422 of body portion 400, and provides a fluid-tight seal in the channel 420 between the lower end 424 and the upper end 422 such that bodily fluids exiting from the punctured skin of the subject being treated will be prevented from travelling from the needle tip portion 210 to the upper end 244 of shaft 240 through the inner channel 420. The seal also prevents ink from entering and passing through the upper end 422 of needle housing 400. The seal thus conveniently prevents the subject's bodily fluids and ink from contacting the drive shaft 35 or base 30. Conveniently, base 30 and drive shaft 35 may be reused after each treatment or after changing the needle module, without the need to re-sterilize them or the entire ink applicator 60. Another convenient effect is that biasing member 300 provides both a biasing function and a sealing function.

It can now also be appreciated that the above convenient effects can also be achieved with different embodiments or variations of the biasing member 300 as depicted in the drawings.

Figure 9A:
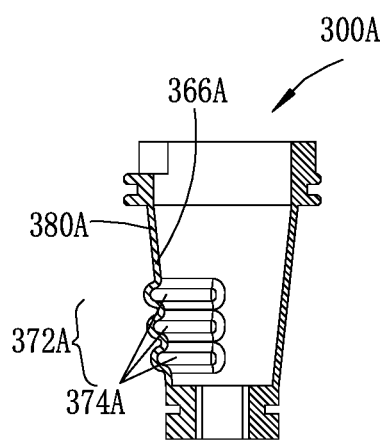
FIGS. 9A, 9B, 9C and 9D are side elevation views of various variants of the biasing member shown in FIGS. 4A to 4C, illustrative of different embodiments of the present disclosure.

For example, FIG. 9A illustrates a variant of the biasing member 300, denoted as 300A, with a partially corrugated side 366A. The other side, the half side opposite side 366A, is generally flat as depicted in FIG. 9A. As depicted in FIG. 9A, side 366A has a corrugated segment 372A and a flat segment 380A. The corrugations 374A on corrugated segment 372A may extend circumferentially by an angle of around 180° around the axial direction of biasing member 300A.

Figure 9B:
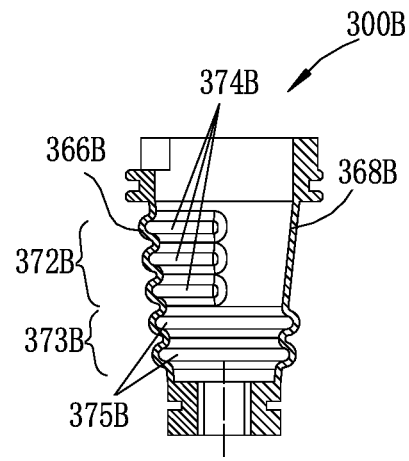

FIG. 9B illustrates another variant, biasing member 300B, with a fully corrugated side 366B and a partially corrugated side 368B. As illustrated in FIG. 9B, the biasing member 300B has a corrugated segment 372B and a corrugated segment 373B. The corrugations 374B on corrugated segment 372B extend circumferentially by an angle of around 180° (about half circle) around the axial direction of biasing member 300B. The corrugations 375B on corrugated segment 373B extend around the entire circumference of biasing member 300B. Side 368B of biasing member 300B is thus partially corrugated while side 366B is fully corrugated.

Figure 9C:
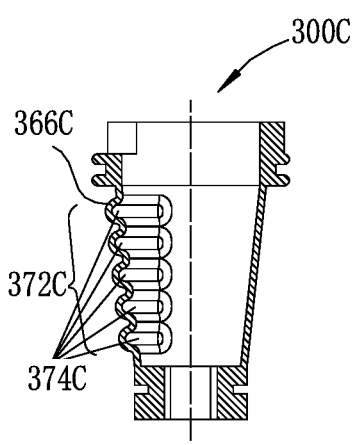

FIG. 9C illustrates a further variant, biasing member 300C. Side 366C of the biasing member 300C has a corrugated segment 372C while the side opposite side 366C is generally flat. The corrugations 374C on corrugated segment 372C extend circumferentially around the axial direction of biasing member 300D by an angle of less than 180°. For example, the corrugations 374C may extend circumferentially by an angle of about 120°.

Figure 9D:
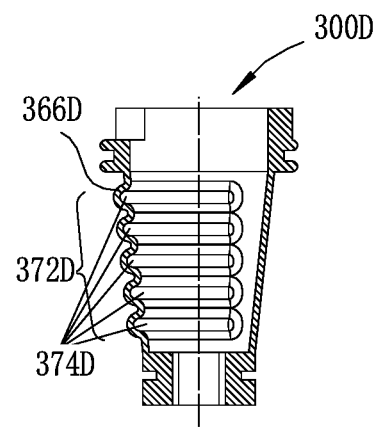

FIG. 9D illustrates another variant, biasing member 300D, with a corrugated side 366D having a corrugated segment 372D. The corrugations 374D of corrugated segment 372D extend circumferentially by an angle of more than 180° around the axial direction of biasing member 300D. For example, the corrugations 374D of corrugated segment 372D may extend circumferentially by an angle of about 240°.

As described herein, the circumferential angle refers to the angle formed by two lines from the center of a circle to two points on the circumference of the circle. It should be noted that, however, in practice, the parts in the disclosed devices may not have perfect circular shapes, and the profiles of the parts may be generally circular and the angles may be approximate.

As can be appreciated, a needle assembly described herein may be used or adapted to apply other types of liquids to skin. For example, the applied liquid may include colored liquids or pigments, or may include a medicinal or therapeutic agent, collagen, or other like or similar substances. The needle assembly may be used in a liquid applicator for applying the selected liquid.

Other features, modifications, and applications of the embodiments described here may be understood by those skilled in the art in view of the disclosure herein.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims.

List of references and corresponding elements as shown in the figures

| Reference Number | Corresponding element |
|---|---|
| 10 | Needle Module |
| 20 | Handle |
| 30 | Base Device |
| 35 | Drive shaft |
| 40 | Housing |
| 60 | tattooing device |
| 100 | Mouthpiece |
| 120 | Opening |
| 122 | Needle-guiding wall |
| 110 | Ink storage grooves |
| 125 | Ink storage groove walls |
| 200 | Needle Bundle |
| 210 | Needle Tip portion |
| 220 | Needle shaft portion |
| 240 | Shaft |
| 242 | Lower end of shaft |
| 244 | Upper end of shaft |
| 246 | Body of shaft |
| 248 | Bore of shaft |
| 250 | Key profile |
| 256 | Outer surface of key profile |
| 260 | Stopper (lower) |
| 262 | Lower surface of lower stopper |
| 270 | Stopper (upper) |
| 274 | Upper surface of upper stopper |
| 300 (A-D) | Biasing Member |
| 320 | Lower end portion |
| 322 | Central opening |
| 324 | Groove |
| 326 | Lower segment of lower portion |
| 328 | Upper segment of lower portion |
| 330 | inner surface of the lower portion |
| 340 | Upper portion |
| 342 | Lower annular ridge on upper portion |
| 344 | Upper annular ridge on upper portion |
| 348 | Keyway |
| 350 | Opening of the upper end portion |
| 352 | Inner wall of the upper end portion |
| 354 | Outer wall of upper end portion |
| 356 | Lower surface of upper portion |
| 358 | Upper surface of upper portion |
| 360 | Tubular section |
| 366 (A-D) | Second side |
| 368 (A-D) | First side |
| 370 | Axial channel of tubular section 360 |
| 372 (A-D) | Corrugated segment |
| 373B | corrugated segment |
| 374 (A-D) | Corrugations |
| 375B | corrugations |
| 380A | smooth section on first side |
| 400 | Tubular body portion |
| 402 | Observation window |
| 420 | Channel |

-continued

| Reference Number | Corresponding element |
|---|---|
| 422 | Upper open end |
| 424 | Lower open end |
| 430 | Keyway |
| 440 | Ridges |
| 450 | Inner wall |
| 470 | Annular ledge |
| 500 | Cap |
| 520 | Channel |
| 530 | Lower channel |
| 532 | Inner wall of lower channel |
| 540 | Upper channel |
| 542 | Inner wall of upper channel |
| 550 | Shoulder between lower channel and upper channel |
| 552 | Lower surface of shoulder |
| 560 | Lower segment of cap |
| 562 | Outer wall of lower segment |
| 564 | Annular rim |
| 566 | Key profile on lower segment 560 |
| 568 | Tapered edge |
| 570 | Middle segment of cap |
| 572 | Lower surface of middle segment |
| 580 | Key profile on middle segment 570 |
| 582 | Groove |
| 590 | Upper segment of cap |
| 810 | Inner assembly |
| 820 | Outer assembly |

What is claimed is:

1. A needle assembly for a liquid applicator, comprising:
a housing comprising a longitudinal channel, the channel comprising an upper open end and a lower open end;
a needle bundle movably mounted in the channel to reciprocatively move between a retracted position and an extended position, the needle bundle comprising a needle shaft and a plurality of needles attached to the needle shaft, the needles positioned to extend through the lower open end of the channel when the needle bundle is in the extended position, the needle shaft received in the upper open end of the channel for driving the needle bundle longitudinally;
a biasing member configured and mounted for (i) biasing the needle bundle longitudinally towards the retracted position and (ii) biasing the needles laterally towards a needle-guiding side wall of the housing adjacent the lower open end, the biasing member being further configured and mounted to form a fluid seal between the lower open end and the upper open end, wherein the biasing member comprises an elastic tubular section having a first side and a second curved side opposite the first side, the first side of the elastic tubular section facing the needle-guiding side wall and having a first rectified length, the second side of the elastic tubular section having a second rectified length longer than the first rectified length so that the second side is less tensioned than the first side to bias the needles towards the needle-guiding side wall.

2. The needle assembly of claim 1, wherein the elastic tubular section has a substantially uniform wall thickness.

3. The needle assembly of claim 1, wherein the first side of the elastic tubular section of the biasing member has a first wall thickness, and the second side of the elastic tubular section of the biasing member has a second wall thickness less than the first wall thickness.

4. The needle assembly of claim 3, wherein the biasing member has first and second end portions, each one of the first and second end portions has a wall thickness larger than the first and second wall thicknesses, and is more rigid than the elastic tubular section.

5. The needle assembly of claim 1, wherein the second side of the elastic tubular section of the biasing member is at least partially corrugated.

6. The needle assembly of claim 1, wherein the elastic tubular section of the biasing member has a first end and a second end, and the biasing member comprises a first end portion attached to the first end of the elastic tubular section and a second end portion attached to the second end of the elastic tubular section, each one of the first and second end portions having a central opening, the needle shaft extending through the central opening, wherein the needle shaft sealingly engages the central opening of the first end portion of the biasing member, and the second end portion of the biasing member is sealingly affixed to the housing so that when the needle bundle moves towards the extended position, the elastic tubular section of the biasing member is tensioned to bias the needle bundle towards the retracted position and bias the needles to contact the needle-guiding side wall.

7. The needle assembly of claim 6, wherein the first end portion of the biasing member comprises a circumferential groove to reduce tension in the first end portion.

8. The needle assembly of claim 6, wherein the first end portion of the biasing member has a generally polygonal cross-sectional profile.

9. The needle assembly of claim 8, wherein the polygonal cross-sectional profile is a square cross-sectional profile.

10. The needle assembly of claim 6, wherein the needle bundle has a key profile around the needle shaft and the central opening of the first end portion of the biasing member defines a keyhole engaged with the key profile of the needle bundle.

11. The needle assembly of claim 10, wherein the needle bundle comprises a key shoulder adjacent the key profile, the key shoulder abutting the first end portion of the biasing member so that the biasing member biases the key shoulder and the needle bundle towards the upper open end of the housing.

12. The needle assembly of claim 6, wherein the housing comprises a removable annular cap at the upper open end of the channel, the cap engaging the second end portion of the biasing member to affix the second end portion to the housing, the cap comprising a central opening, the needle shaft passing through the central opening of the cap.

13. The needle assembly of claim 12, wherein the housing comprises a first keyway at the upper open end, the second end portion of the biasing member comprises a second keyway, and the cap comprises a first key profile coupled with the first keyway of the housing and a second key profile coupled with the second keyway of the biasing member.

14. The needle assembly of claim 12, wherein the upper open end of the housing comprises an internal annular ridge and the cap comprises an annular groove coupled to the annular ridge to hold the cap in position.

15. The needle assembly of claim 1, wherein the biasing member forms a diaphragm seal between the lower open end and the upper open end of the housing.

16. The needle assembly of claim 1, wherein the first side of the elastic tubular section is substantially linear.

17. The needle assembly of claim 1, wherein at least a portion of the first side of the elastic tubular section is curved.

18. The needle assembly of claim 1, wherein the biasing member comprises a silicone material, latex or a rubber.

19. The needle assembly of claim 1, wherein the biasing member comprises a material with a Shore hardness from 30 A to 50 A.

20. The needle assembly of claim 1, wherein the housing comprises a liquid storage groove at the needle-guiding wall adjacent the lower open end.

21. The needle assembly of claim 1, configured to apply tattoo or permanent make-up to skin.

22. The needle assembly of claim 1, wherein the needle assembly is a disposable module.

23. A liquid applicator comprising the needle assembly of claim 1.

24. The liquid applicator of claim 23, further comprising a needle actuator, and a handle coupling the needle actuator to the needle assembly.

* * * * *